Figure 1:
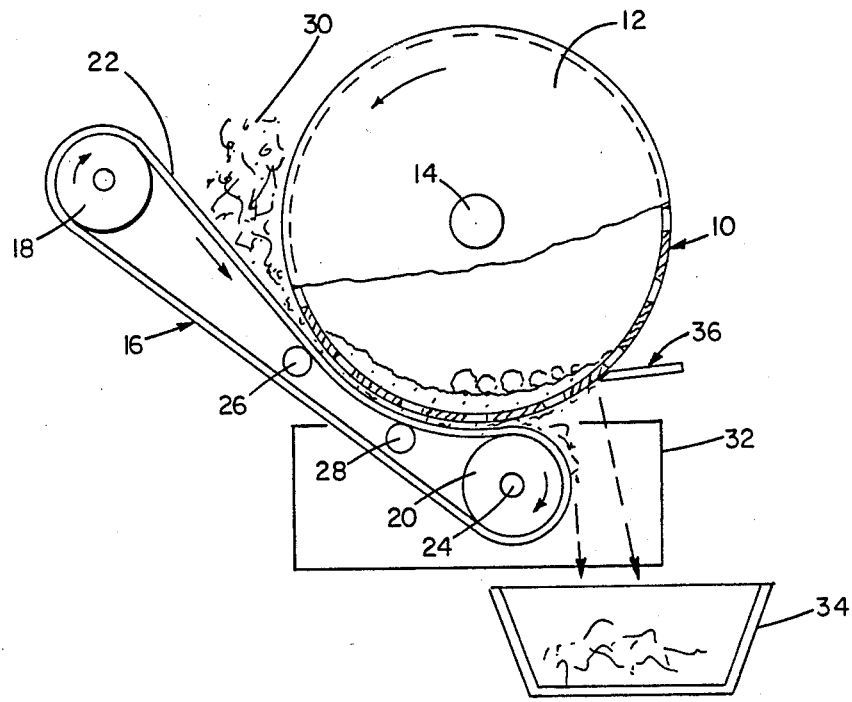

United States Patent [19]
Whitaker

[11] Patent Number: 4,765,886
[45] Date of Patent: Aug. 23, 1988

[54] METHOD FOR SEPARATING SEA PLANTS

[75] Inventor: R. John Whitaker, Cornwall, Canada

[73] Assignee: Carratech, Inc., Charlottetown, Canada

[21] Appl. No.: 862,664

[22] Filed: May 13, 1986

Related U.S. Application Data

[63] Continuation-in-part of Ser. No. 801,579, Nov. 25, 1985.

[51] Int. Cl.⁴ .............................................. B03B 1/04
[52] U.S. Cl. ........................................ 209/2; 209/7; 209/235
[58] Field of Search .............. 536/3; 209/240, 243, 209/270, 272, 279, 280, 284, 285, 200, 683, 686, 2, 7, 235

[56] References Cited

U.S. PATENT DOCUMENTS

| | | | |
|---|---|---|---|
| 1,620,439 | 3/1929 | Carter | 209/285 |
| 3,423,397 | 1/1969 | Hasaini | 536/3 |
| 4,104,460 | 8/1978 | Hasebe | 536/3 |
| 4,469,230 | 9/1984 | Gorlitz | 209/683 |
| 4,474,951 | 10/1984 | Pope | 536/3 X |

FOREIGN PATENT DOCUMENTS 643461  1/1961  Italy .................................. 209/683

OTHER PUBLICATIONS

Brochure entitled "SDX 18 Meat Separator" by Bibun Machine Construction Co. Ltd."
Brochure entitled "Baader 694 Bone Separator" by Nordischer Maschinenbau Rud. Baader.

*Primary Examiner*—David A. Scherbel

[57] ABSTRACT

A mixture of sea plants, some of which have compacted sticky characteristics and others of which exhibit hard incompactible fronded characteristics is separated into its components by pressing against a perforated surface to extrude the compacted sticky material through the perforations.

4 Claims, 1 Drawing Sheet

METHOD FOR SEPARATING SEA PLANTS

This application is a continuation-in-part of Whitaker Ser. No. 801,579 filed Nov. 25, 1985.

This invention relates to an improved method of separating sea plants containing lambda-carrageenan from those containing kappa-carrageenan and pertains more specifically to an extrusion procedure for said separation.

Carrageenan, a polysaccharide hydrocolloid obtained from sea plants has long been known to exist primarily in chemically different species: kappa-carrageenan which is caused to gel or precipitate from aqueous solution by the addition of potassium and certain other ions; and lambda-carrageenan which remains soluble in aqueous solutions of potassium salts. Because of their differing gelling characteristics and their consequent different practical utilities, it has become important to separate these two forms of carrageenan and to provide each of them in substantially pure form as an article of commerce. However, as sea plants occur in nature and as they are commonly harvested, the plants contain varying proportions of kappa- and of lambda-carrageenan.

It has previously been proposed in my U.S. Pat. application Ser. No. 801,579 filed Nov. 25, 1985, to treat mixtures of sea plants, for example of the genus *Chondrus crispus* (also called Irish moss) with certain aqueous media so that the lambda-carrageenan-bearing plants, the diploid form, (hereinafter "lambda plants") preferentially absorb water and exhibit compacted sticky characteristics while the kappa-carrageenan-bearing plants, the haploid form, (hereinafter "kappa plants") retain their hard incompactable fronded characteristics, and can be separated, for example, by visual inspection and manual separation or otherwise.

It has been found that conventional machines for separating bones from fish can be effectively used for separating lambda plants from kappa plants in a mixture after treatment of the mixture to hydrate the lambda plants as described above. Such machines generally comprise a perforated surface against which the fish material to be separated is pressed so that a selected portion of the material is extruded through the perforations.

The present invention comprises an improvement in the method of separating lambda-carrageenan-containing sea plants from kappa-carrageenan-containing sea plants in a mixture of said plants which comprises treating said mixture to preferentially hydrate the first said plants in said mixture until they exhibit compacted sticky characteristics while the second said plant retain their hard incompactible fronded characteristics, the improvement comprising pressing said treated mixture against a perforate surface to extrude the first said plants through said perforations while leaving the second said plants on said perforate surface, and separating the second said plants from said perforate surface.

Figure 2:
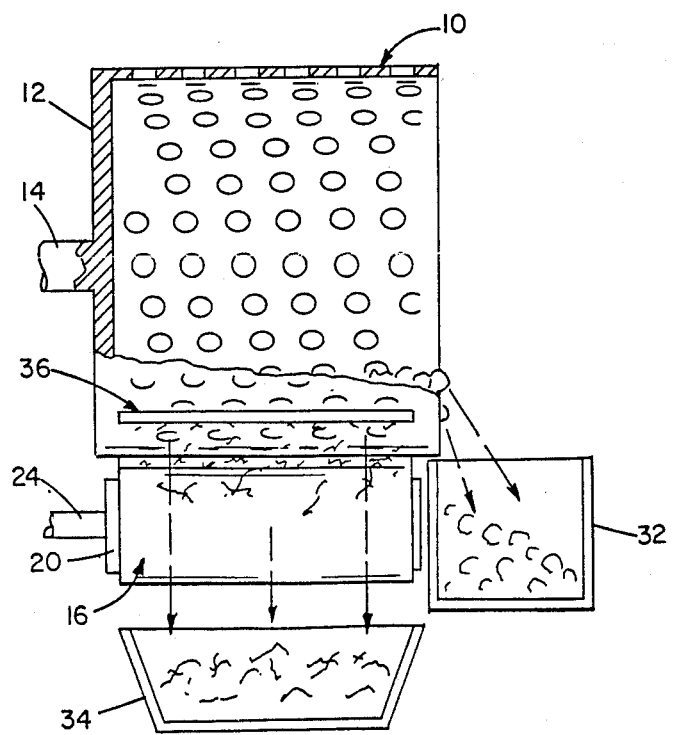

In the drawing,

FIG. 1 is a schematic view in section of a machine for carrying out the method of the present invention; and FIG. 2 is a view in front elevation.

The method is carried out by first maintaining a mixture of kappa- and lambda-carrageenan-containing plants in contact with a water solution at a pH above about 10. The water solution contains a cation selected from the group consisting of ammonium, potassium, rhubidium, cesium, calcium, barium, strontium and magnesium, preferably potassium or calcium, the initial concentration of the cation being at least 0.0025 molar, preferably from 0.0025 to 0.2 molar, and the temperature is maintained within the range from 5° to 95° C. until the lambda plants exhibit compacted sticky characteristics while the kappa plants retain their hard incompactible fronded characteristics. In such a treated mixture the water content of the lambda plants is from 4.5 to 15, preferably 4.5 to 7, times the bone-dry weight, and the water content of the kappa plants is no greater than 6, preferably no greater than 4 times the bone-dry weight. By "bone dry weight" is meant the value achieved by heating a sample in a circulating hot air oven at 70° C. until the sample achieves constant weight.

The machine into which the thus treated mixture is fed, as appears from the drawings, comprises a perforated metal drum 10 mounted on spider 12 fixed to shaft 14 rotated by a suitable drive mechanism (not shown). A pressure conveyor belt 16 is mounted on spaced rolls 18,20 with reach 22 of the belt pressed against the outer surface of drum 10. Although rolls 18,20 may be idler rolls so that the belt is advanced solely by frictional engagement with the surface of drum 10, it is preferred that roll 20 be driven by suitable mechanism (not shown) so that the belt advances at the same linear speed as the surface of drum 10. Cam 24 is provided to adjust the pressure exerted against the drum. Idler rolls 26,28, together with mechanism (not shown) for moving roll 18 toward and away from drum 10 serve to help maintain tension on the belt, hence its pressure against surface of drum 10. These features also assist in adjusting, the length of the belt in contact with the drum surface and aid in smoothing out irregularities and lumpiness in the feed of sea plants between the belt and the drum.

In carrying out the method of the invention, the treated mixture of sea plants 30 is introduced into the nip between belt reach 22 and drum 10 while the drum is rotating. The pressure provided by the belt forces the lambda plants to extrude through the perforations in the drum, where it eventually forms balls of sticky plant material which discharge by gravity from the open end of the drum 10 into a suitable receptacle 32.

The kappa plant which is not forced through the perforations because of its inherently stronger and more resilient characteristics falls away from the surface of drum 10 and belt 16, dropping into container 34. In order to ensure complete removal of the kappa plant from the surface of the drum, a scraper or doctor blade 36 may be provided. If desired, the kappa plant can be recycled through the apparatus. The perforations may range in diameter from about 1 to about 3 mm, and the drum is preferably of heavy gauge (10 mm) metal construction. The pattern or distribution of the perforations is not critical, although they are preferably spaced apart by at least a distance equal to the perforation diameter, except as it affects the capacity of the apparatus and/or its speed of operation. It is desirable to coordinate the speed of rotation of drum 10, the size and distribution of perforations, the length of the reach of belt 16 pressing against the drum, and the pressure exerted in order to achieve optimum results for any given treated mixture of sea plants. The method involves a continuous pressure sieving or straining operation, the lambda plants being forced through the sieve while the kappa plants are retained on its surface.

It has been found that in the case of a plant mixture containing 35% lambda plant and 65% kappa plant, with suitable adjustment of the apparatus, the lambda plant material obtained from the inside of the rotating drum contains less than 5% by weight of kappa plant, while the kappa plants removed from the external surface of the drum contain less than 5% by weight of lambda plant material.

What is claimed is:

1. The method of separating lambda-carrageenan-containing sea plants from kappa-carrageenan-containing sea plants in a mixture of said plants which comprises treating said mixture with an aqueous solution at a pH above about 10 and at a temperature from 5° to 95° C., said solution containing a cation selected from the group consisting of ammonium, potassium, rubidium, cesium, calcium barium, strontium and magnesium to preferentially hydrate the first said plants in said mixture until they exhibit compacted sticky characteristics while the second said plants retain substantially their hard incompactible fronded characteristics, pressing said treated mixture against a perforate surface to extrude the first said plants through said perforations while leaving the second said plants on said perforate surface, and separating the second said plants from said perforate surface.

2. The method as claimed in claim 1 in which said perforate surface comprises a rotating drum and the treated mixture is pressed against said drum at it rotates.

3. The method as claimed in claim 2 in which the perforations in said drum are from about one to about three millimeters in diameter.

4. The method of separating lambda-carrageenan-containing sea plants from kappa-carrageenan-containing sea plants in a mixture of said plants which comprises treating said mixture with an aqueous solution at a pH above about 10 and at a temperature from 5° to 95° C., said solution containing a cation selected from the group consisting of ammonium, potassium, rubidium, cesium, calcium barium, strontium and magnesium to preferentially hydrate the first said plants in said mixture until they exhibit compacted sticky characteristics while the second said plants retain substantially their hard incompactible fronded characteristics, and subjecting said treated mixture to a continuous pressure sieving to force the first said plants through the sieve while retaining the second said plants on the sieve surface.

* * * * *